United States Patent
Meislin et al.

(10) Patent No.: US 10,792,035 B2
(45) Date of Patent: Oct. 6, 2020

(54) COMBINED TISSUE GRASPER-SUTURE RETRIEVER INSTRUMENT AND METHOD OF TISSUE REPAIR

(71) Applicant: Arthrex, Inc., Naples, FL (US)

(72) Inventors: Robert J. Meislin, New York, NY (US); Jacob A. Jolly, Naples, FL (US)

(73) Assignee: ARTHREX, INC., Naples, FL (US)

( * ) Notice: Subject to any disclaimer, the term of this patent is extended or adjusted under 35 U.S.C. 154(b) by 457 days.

(21) Appl. No.: 14/697,212

(22) Filed: Apr. 27, 2015

(65) Prior Publication Data

US 2016/0310132 A1    Oct. 27, 2016

(51) Int. Cl.
| A61B 17/04 | (2006.01) |
| A61B 17/00 | (2006.01) |
| A61B 17/29 | (2006.01) |

(52) U.S. Cl.
CPC ...... *A61B 17/0483* (2013.01); *A61B 17/0485* (2013.01); *A61B 17/29* (2013.01); *A61B 2017/00353* (2013.01)

(58) Field of Classification Search
CPC ............ A61B 17/0482; A61B 17/0483; A61B 17/0469; A61B 2017/00353; A61B 17/29; A61B 17/0485; A61B 17/0496; A61B 17/28; A61B 17/2812; A61B 17/282; A61B 2017/2926
See application file for complete search history.

(56) References Cited

U.S. PATENT DOCUMENTS

| 7,585,305 B2 | 9/2009 | Dreyfuss | |
| 2003/0233106 A1* | 12/2003 | Dreyfuss | A61B 17/0469 606/144 |
| 2008/0009900 A1 | 1/2008 | Heaven et al. | |
| 2009/0312794 A1* | 12/2009 | Nason | A61B 17/0401 606/232 |
| 2010/0121352 A1* | 5/2010 | Murray | A61B 17/0469 606/144 |
| 2015/0012016 A1* | 1/2015 | Stone | A61B 17/0469 606/144 |

FOREIGN PATENT DOCUMENTS

WO    WO 2014/172589 A1    10/2014

OTHER PUBLICATIONS

Microline Surgical, Confidence Simply Delivered, Laparoscopic Surgical Instrumentation, 3381 10mm Babcock, www.microlinesurgical.com, 2009.

* cited by examiner

Primary Examiner — Wade Miles
Assistant Examiner — Mikail A Mannan
(74) Attorney, Agent, or Firm — Carlson, Gaskey & Olds

(57) ABSTRACT

A combined tissue grasper and suture retriever instrument and methods for surgical repairs are disclosed. An instrument allows grasping of tissue with simultaneous passage of a flexible strand from a suture passer.

24 Claims, 2 Drawing Sheets

COMBINED TISSUE GRASPER-SUTURE RETRIEVER INSTRUMENT AND METHOD OF TISSUE REPAIR

BACKGROUND

The present disclosure relates to surgical instruments for grasping and suturing tissue and methods of tissue repair. In particular, the present disclosure relates to a combined tissue grasper-suture retriever instrument.

SUMMARY

A combined tissue grasper and suture retriever instrument and techniques for surgical repairs are disclosed. A tissue grasper-suture retriever can hold tissue (e.g., torn meniscal root) in place while simultaneously allowing a flexible strand from a separate suture passer or suture lasso to pass through the tissue and through perforations in the jaws of the tissue grasper-suture retriever. The jaws can include a feature that can capture a flexible strand and lock it into place. In an embodiment, the feature may be a tear drop-shaped perforation or through-opening in one of the jaws. A grasper can be flat and wide to allow effective grasping and pulling of tissue.

A tissue grasper-suture retriever device allows grasping of tissue with simultaneous passage of a flexible strand (suture strand or wire) from a suture passer through perforation in the jaws.

A method of grasping and suturing tissue is also disclosed. In an embodiment, tissue can be grasped and sutured with a single combined tissue grasper and suture passer instrument. In an illustrative embodiment, injured meniscal tissue can be grasped and sutured with a single combined tissue grasper and suture passer instrument.

DETAILED DESCRIPTION

Figure 1:
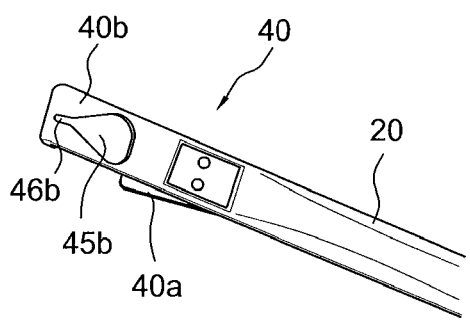
FIG. 1 is a perspective view of a distal end of a combined tissue grasper and suture passing instrument according to an exemplary embodiment.

A combined suture passer and tissue grasper instrument and surgical techniques for endoscopic surgical repairs, for example, arthroscopic surgeries, are disclosed herein. A combined tissue grasper and suture passer instrument allows simultaneous gripping or grasping of tissue (e.g., meniscal tissue) while allowing a flexible strand (for example, suture, suture wire, or a nitinol wire loop) provided by a different instrument to pass through jaws of a combined instrument and through a tissue grasped with a combined instrument.

A grasper is also disclosed. A grasper can be flat and wide allowing effective grasping and pulling of tissue. A grasper can have a through hole, opening, or perforation in the upper jaw with a suture or wire catching feature. For example, a tear drop shaped hole allows a suture or wire to be wedged into a grasper when pulling the grasper out of a joint. A bottom jaw can have an opening as well, and the opening can extend to the end of the jaw (i.e., communicates with an outer circumference of the lower jaw) to allow a suture to slip out. In an illustrative embodiment, an opening in a bottom jaw allows a flexible strand (e.g., suture) to be released once the flexible strand passes through tissue.

Certain tissues such as torn meniscal roots are difficult to reduce over their origin while simultaneously piercing the tissue with an instrument and retrieving suture. "Lasso"-type devices and the like require large portals to accommodate the instruments, particularly at work sites that are too small to accommodate such instruments. Combined tissue grasper and suture passing instruments disclosed herein allow a surgeon to quickly, accurately, and easily pass suture through tissues without requiring large portals at a surgical site to accommodate such suture passing instruments. For example, a disclosed combined grasper-suture retriever instrument and method of using such instrument can reduce a torn meniscal root over its origin while simultaneously piercing the tissue with the instrument and retrieving suture.

An exemplary grasper-suture retriever instrument comprises: a shaft having a longitudinal axis, a distal end, and a proximal end; a stationary first jaw at the distal end of the shaft, the first jaw having a first through opening to allow a flexible strand (provided by a separate instrument) to pass therethrough, and a transversal slot or passage extending from an outer circumference of the first jaw to the first through opening to allow the flexible strand to slide out of the first jaw; a second jaw mounted to the distal end of the shaft and pivotally connected to the first jaw such that the second jaw is moveable with respect to the first jaw from an open position to a closed position, the second jaw comprising a second through opening with a securing mechanism to secure the flexible strand at its most distal end; and a handle configured to move the second jaw with respect to the first jaw.

Another embodiment of a grasper-suture retriever instrument includes: a shaft having a longitudinal axis, a distal end, and a proximal end; a stationary first jaw at the distal end of the shaft, the first jaw having a first through opening to allow a flexible strand (provided by a separate instrument) to pass therethrough, and a transversal slot or passage extending from an outer circumference of the first jaw to the first through opening to allow the flexible strand to slide out of the first jaw; a second jaw mounted to the distal end of the shaft and pivotally connected to the first jaw such that the second jaw is moveable with respect to the first jaw from an open position to a closed position, the second jaw comprising a second through opening with a securing mechanism to secure the flexible strand at its most distal end; and an actuator configured to move at least one of the first and second jaws. An actuator can be within the shaft and at the distal end of the shaft.

A method of grasping and suturing tissue is also disclosed. In an embodiment, tissue can be grasped and sutured with a single combined tissue grasper and suture passer instrument, for example a combined tissue grasper and suture passer instrument as disclosed herein. In an embodiment, a portion of tissue can be grasped and sutured with a single combined tissue grasper and suture passer instrument. In an illustrative embodiment, injured meniscal tissue can be grasped and sutured with a single combined tissue grasper and suture passer instrument.

In an embodiment, a method of grasping and suturing tissue includes grasping or gripping at least a portion of tissue. In an embodiment, a method of grasping and suturing tissue includes passing a flexible strand through a bone tunnel adjacent to an articular surface and tissue, through lower and upper jaws of a combined suture passer and tissue grasper, and through the tissue grasped or gripped by the lower and upper jaws. In an illustrative embodiment, a method of grasping and suturing tissue includes capturing a flexible strand onto a jaw of a combined tissue grasper and suture passer and releasing a flexible strand from the other jaw. In an illustrative embodiment, a flexible strand is released from a jaw once the flexible strand passes through tissue. In an embodiment, an opening on a jaw allows for the flexible strand to be released once the flexible strand passes through tissue.

An exemplary method of grasping and suturing tissue comprises: (i) grasping or gripping at least a portion of a tissue with a combined grasper-suture passing instrument; (ii) passing a flexible strand through a bone tunnel adjacent to an articular surface and tissue, through lower and upper jaws of the instrument, and through the tissue grasped or gripped by the lower and upper jaws; (iii) capturing the flexible strand onto one of the jaws; and (iv) releasing the flexible strand from the other jaw.

In an illustrative embodiment, a method of grasping and suturing tissue includes grasping or gripping at least a portion of an injured meniscus. In an illustrative embodiment, at least a portion of injured meniscus can be grasped or gripped by a combined suture passer and tissue grasper. In an embodiment, a method of grasping and suturing meniscus includes passing a flexible strand through a bone tunnel adjacent to an articular meniscal surface and tissue, through lower and upper jaws of a combined suture passer and tissue grasper instrument, and through the tissue grasped or gripped by the lower and upper jaws. In an illustrative embodiment, a method of grasping and suturing tissue includes capturing a flexible strand onto a jaw of a combined tissue grasper and suture passer and releasing the flexible strand from the other jaw once passed through the meniscus. In an illustrative embodiment, a bone tunnel can be a tibial bone tunnel.

The term "endoscopy" refers to arthroscopy, laparoscopy, hysteroscopy, etc.

The term "endoscopic surgery" refers to surgical procedures within a patient's body through small openings as opposed to conventional open surgery through large incisions.

Figure 5:
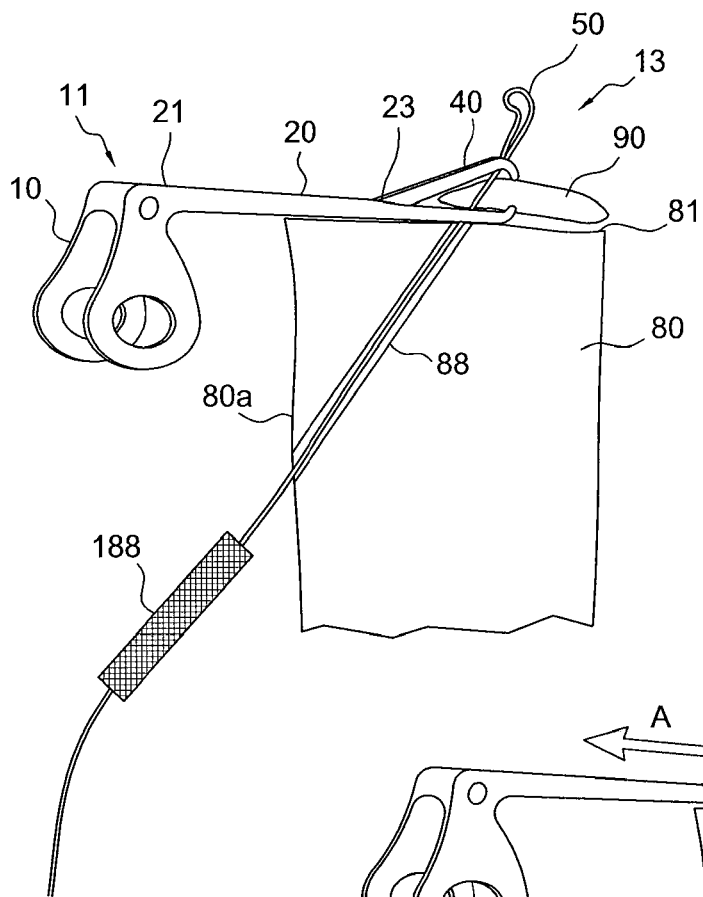
FIGS. 5-7 illustrate an exemplary method of meniscal repair with a combined tissue grasper and suture passing instrument.
Figure 6:
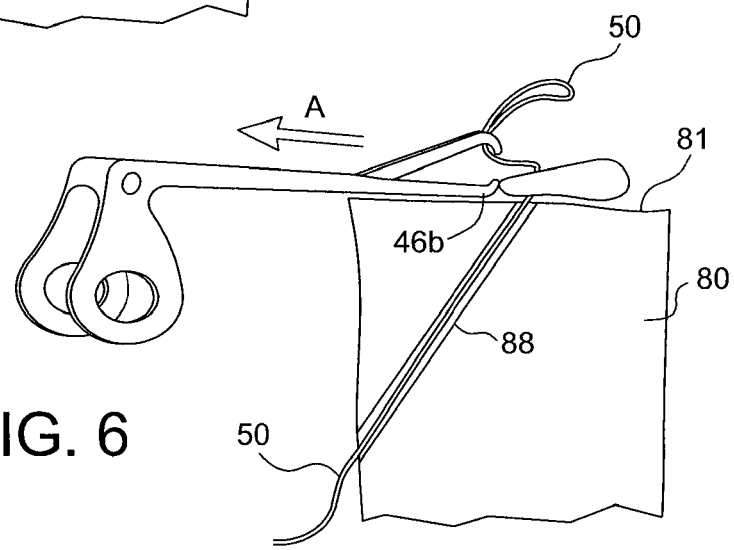
Figure 7:
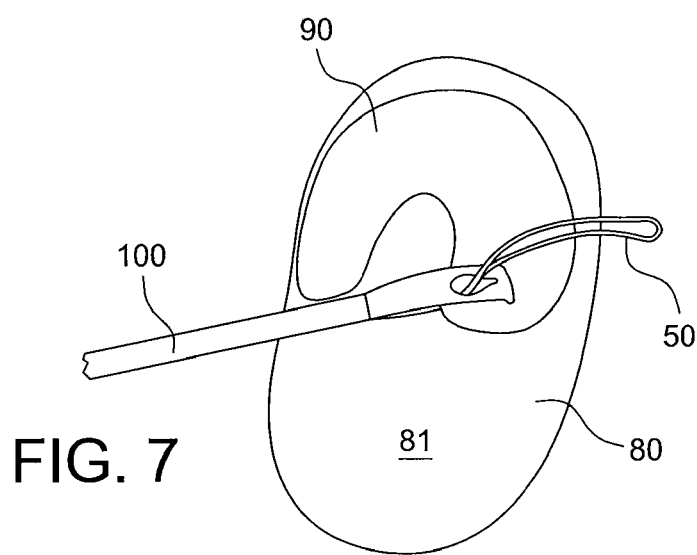

Referring now to the drawings, where like elements are designated by like reference numerals, FIGS. 1-4 illustrate various structural elements of instrument 100 (combined tissue grasper and suture passing instrument 100) provided with a handle 10, an elongated tubular member or shaft 20 having a longitudinal axis 20a, a proximal end 21, a distal end 23 and an axial throughbore therein (not shown), and a pair of jaws 40a, 40b. FIGS. 5-7 illustrate an exemplary method of meniscal repair with instrument 100.

Elongated tubular member 20 may be a tube or a narrow-diameter rod of dimensions that permits the tubular member to be introduced through an associated cannula (for example, an 8.25 cannula) in a minimally invasive procedure, such as arthroscopic or other endoscopic procedures, or into a body cavity, such as the abdominal cavity. Elongated tubular member 20 is formed of a rigid, stiff material such as stainless steel or any rigid, medically acceptable metal or plastic material that does not allow bending or flexing.

Elongated tubular member 20 connects to handle 10 at the proximal end 21 and can be integral with the handle 10. As illustrated in FIG. 1, rigid tubular member 20 is substantially straight with respect to the handle 10 and is fully cannulated. Elongated tubular member 20 connects the handle 10 to a tip 40 consisting of a pair of jaws or jaw members 40a, 40b. The jaws include first and second jaws 40a, 40b (also referred to as lower jaw 40a and upper jaw 40b).

Handle 10 of the instrument 100 (illustrated in FIGS. 5 and 6) is provided at the proximal end 11 of instrument 100 and may include various mechanisms and/or actuators for manipulating the jaws relative to the outer stiff tube 20. For example, handle 10 may be provided with a trigger or actuating mechanism which may consist of a finger lever which, when actuated, is designed to move one of the jaws relative to the outer tube.

Instrument 100 may further include an actuator (not shown). An actuator can be within the shaft 20 and at the distal end of the shaft. A proximal end of an actuator can be pivotally connected to a finger lever and a distal end of the actuator can be pivotally connected to one of the jaws, for example, the upper jaw 40b. An actuator is designed to move one of the jaws (the upper jaw 40b) from a first position to a second position, as a finger lever is moved from a first position to a second position. At a default position of a finger lever, upper jaw 40b may be farthest from the lower jaw 40a.

In an embodiment, first and second jaws 40a, 40b include a lower jaw 40a provided at the distal end 13 of the instrument and preferably stationary, i.e., integral with the tubular member 20. As illustrated in FIG. 5, for example, first jaw 40a (lower jaw 40a) is substantially straight with respect to the shaft, while second jaw 40b (upper jaw 40b) is designed to pivot with respect to the lower jaw 40a.

Figure 2:
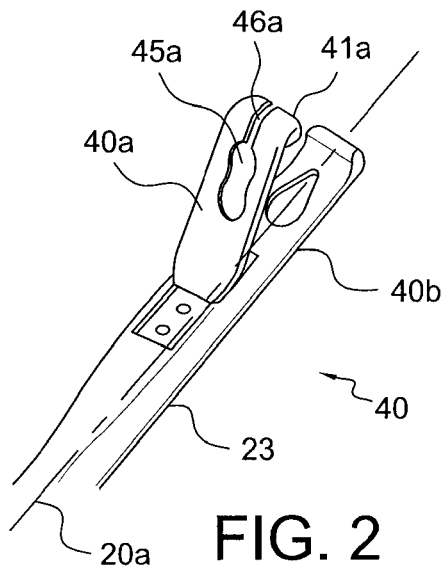
FIG. 2 is another perspective view of the distal end of the instrument of FIG. 1.
Figure 3:
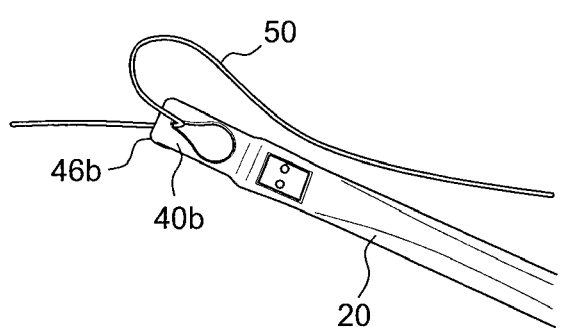
FIGS. 3 and 4 illustrate capturing a suture with the instrument of FIG. 1.
Figure 4:
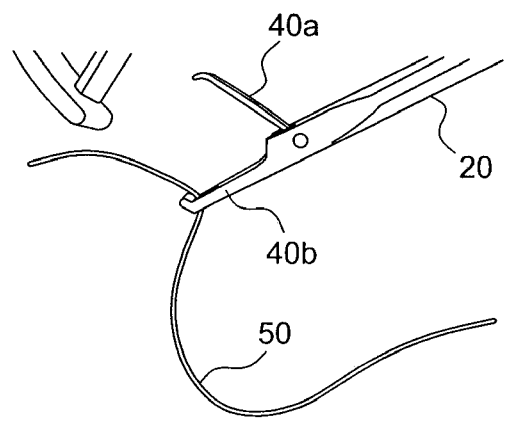

In an exemplary embodiment, and as shown in FIG. 2, first jaw 40a has a first through opening 45a to allow a flexible strand 50 to pass therethrough, and a transversal slot 46a or passage 46a extending from an outer circumference 41a of the first jaw 40a to the first through opening 45a, to allow the flexible strand 50 to easily slide out of the first jaw 40a (as shown in FIG. 4), for example, when the instrument is pulled out of a joint and away from a repair site.

As shown in FIG. 1, for example, the second jaw 40b is mounted to the distal end 23 of the shaft 20 and is pivotally connected to the first jaw 40b such that the second jaw 40b is moveable with respect to the first jaw 40a from an open position to a closed position (or from a first position to a second position, which is different from the first position). Further, the second jaw 40b includes a second through opening 45b with a securing mechanism 46b to secure flexible strand 50 at the most distal end of jaw 40b. In an exemplary embodiment, a securing mechanism 46b can be a transversal slot, and the second through opening 45b can have an exemplary tear drop shape.

The first and second jaws 40a, 40b may each include a plurality of teeth for gripping or grasping tissue (such as meniscal tissue 90 illustrated in FIGS. 5-7).

In use, and as detailed below, the handle 10 can be configured to move one jaw with respect to the other jaw (for example, the second jaw with respect to the first jaw). Thereby, an instrument can securely grasp tissue 90 with the two jaws 40a, 40b. The tissue may be torn meniscus to be repaired and/or reattached to an articular surface 81 (e.g., knee). Flexible strand 50 (in an exemplary form of a wire loop 50) can be provided from a different instrument or device 188 (for example, a suture passer instrument) and passed through a bone tunnel 88, through tissue 90, and through openings 45a, 45b. Bone tunnel 88 can be formed within tibia and can extend between cortical tibial surface 80a and articular surface 81. When the instrument 100 is pulled out of a knee joint in the direction of arrow A (FIG.

6), flexible strand 50 will slide out of transversal slot 46a but will remain secured within securing mechanism 46b of jaw 40b.

A surgical instrument described above and with reference to FIGS. 1-4 may be employed in various surgical medical procedures for grasping or gripping tissue while simultaneously retrieving, transferring, treating, closing, and/or tightening sutures and suture loops during surgical procedures. For example, a tissue grasper and suture retrieving instrument may be employed in endoscopic and arthroscopic procedures, including but not limited to meniscal repair, arthroscopic rotator cuff repair, Bankhart shoulder repair, and any orthopedic procedure that requires manipulation of suture through soft tissue or bone tunnels, or in conjunction with fixation devices, such as suture anchors. Additionally, a tissue grasper and suture retrieving instrument may be utilized in other general surgical and specialty procedures that require grasping and suturing at a remote site, such as inside the body. A tissue grasper-suture retriever instrument as described herein may be also used in repairs where suture visibility or finger access can be limited.

In an illustrative embodiment, and with reference to FIGS. 5-7, a method of suturing tissue using a tissue grasper and suture passing instrument 100 comprises, inter alia, the steps of: (i) grasping or gripping at least a portion of the tissue 90 with jaws 40a, 40b of a combined tissue grasper-suture passing instrument 100; (ii) passing a flexible strand 50 through a bone tunnel 88 and adjacent to articular surface 81 and tissue 90, through the jaws 40a, 40b of the instrument 100, and through the tissue 90 grasped or gripped by the jaws 40a, 40b; and (iii) pulling the instrument 100 and the flexible strand 50 out of the joint. In an embodiment, the flexible strand 50 is captured onto one of the jaws (while still passed through tissue 90) but is released from the other of the jaws of instrument 100. In an embodiment, the flexible strand 50 is passed with a separate instrument 188.

An exemplary method of grasping and suturing a meniscus using a combined tissue grasper and suture passing instrument 100 comprises, inter alia, the steps of: (i) grasping or gripping at least a portion of meniscal tissue 90 by closing upper and lower jaws 40a, 40b of the combined tissue grasper and suture passing instrument 100; (ii) forming a tibial tunnel 88; (iii) passing a flexible strand 50 through the tibial tunnel 88 through the lower jaw 40a of the instrument, through the meniscal tissue 90, and through and out of the upper jaw 40b of the instrument 100; (iv) actuating the handle 10 to open the jaws 40a, 40b (i.e., to release or to move the upper jaw from a first closed position to a second open position) of the instrument 100; and (v) pulling the instrument 100 out of the knee joint and away from the meniscal tissue 90 (in the direction of arrow A of FIG. 6). In an embodiment, flexible strand 50 is captured in the upper jaw 40b and released from the lower jaw 40a, by passing or sliding the flexible strand 50 from the through opening 45a and through a slot or passage 46a connecting the through opening 45a to an outer circumference 41a of the lower jaw 40a. In an embodiment, the closing of upper and lower jaws 40a, 40b comprises actuating a finger level so that the upper jaw 40b is brought in line with the lower jaw 40a and with a longitudinal axis 20a of the instrument 100. In a further embodiment, the tibial tunnel 88 extends between a cortical surface 80a of the tibia 80 and a knee articular surface 81 of the tibia 80. In another embodiment, step (iii) includes passing the flexible strand 50 from the cortical surface 80a to the knee articular surface 81 of the tibia 80.

Flexible strand 50 may be a suture strand or any suture-like material known in the art, or a suture passing device or suture capturing member (for example, a FiberLink™ (Arthrex Inc., Naples, Fla.), or a Nitinol wire shuttle loop, or a monofilament suture loop, or a snare made of Nitinol wire, or a FiberStick™ (Arthrex) (for example, a #2 FiberWire® (Arthrex) with 12 inches stiffened portion which may be also used with a PushLock® (Arthrex) anchor)) that allows passing of a suture through tissue 90.

Flexible strand 50 may include a high-strength suture, such as an ultrahigh molecular weight polyethylene (UHMWPE) suture. Alternatively, high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material. FiberWire® suture includes a core within a hollow braided construct, the core being a twisted yarn of UHMWPE. If an UHWMPE suture is provided without a core, the UHWMPE suture may be employed in additional splicing steps, as needed.

Flexible strand 50 may be also a stiff suture such as FiberStick™, which may be inserted through a cannulated shaft of the surgical instrument 188 and then through jaws of instrument 100 and tissue 90. The end of a FiberStick™ suture that has been passed through a tissue 90 may then be retrieved and used to tie down the tissue.

What is claimed is:

1. A combined tissue grasper and suture passing instrument comprising:
    a shaft having a longitudinal axis, a distal end, and a proximal end;
    a first jaw integral to the distal end of the shaft, the first jaw having a first through opening to allow a flexible strand to pass therethrough, and a first transversal slot or passage extending from an outer circumference of the first jaw to the first through opening, wherein the first transversal slot or passage opens through the outer circumference to allow the flexible strand to slide out of the first jaw, wherein a widest portion of the first transversal slot or passage is narrower than a widest portion of the first through opening;
    a second jaw mounted to the distal end of the shaft and pivotally connected to the first jaw such that the second jaw is moveable with respect to the first jaw from an open position to a closed position, the second jaw comprising a second through opening and a second transversal slot or passage to secure the flexible strand to the second jaw, the second transversal slot or passage extending from the second through opening and terminating prior to an outer circumference of the second jaw, wherein the second transversal slot or passage is narrower than the second through opening; and
    a handle configured to move the second jaw with respect to the first jaw.

2. The instrument of claim 1, wherein the second through opening has a tear drop shape.

3. The instrument of claim 1, wherein the first and second jaws are each provided with a plurality of teeth.

4. The instrument of claim 1, wherein the flexible strand is a suture.

5. The instrument of claim 1, wherein the flexible strand is a suture capturing member that retains suture.

6. The instrument of claim 5, wherein the suture capturing member is a wire loop, a snare, or a stiff strand of ultrahigh molecular weight polyethylene.

7. The instrument of claim 5, wherein the suture capturing member is a Nitinol wire loop.

8. The instrument of claim 1, wherein the first through opening and the first transversal slot are coaxial with one another along a first central longitudinal axis of the first jaw, and wherein the second through opening and the second transversal slot are coaxial with one another along a second central longitudinal axis of the second jaw.

9. The instrument of claim 1, wherein the first jaw and the second jaw each includes a substantially flat profile that extends between proximal end and a curved distal end.

10. The instrument of claim 1, wherein the first through opening includes a figure eight shape, and the first transversal slot or passage includes a uniform width from the first through opening to the outer circumference of the first jaw.

11. The instrument of claim 1, wherein neither the second through opening nor the second transversal slot or passage opens through the outer circumference of the second jaw.

12. A method of simultaneously grasping and suturing tissue comprising:
grasping or gripping the tissue with the combined tissue grasper and suture passing instrument of claim 1;
advancing the flexible strand through a bone tunnel adjacent to and through the tissue, wherein the flexible strand passes through the first through opening in the first jaw and the second through opening in the second jaw of the instrument; and
locking the flexible strand within the second transversal slot or passage of the second jaw wherein the flexible strand is released from the first jaw.

13. The method of claim 12, wherein the bone tunnel extends from a cortical bone surface to an articular surface of the bone adjacent the tissue.

14. The method of claim 12, wherein the flexible strand passes through the bone tunnel so that the flexible strand exits a first opening at the articular surface of the bone and passes through the tissue and through the first and second through opening of the jaws of the instrument.

15. The method of claim 14, wherein the flexible strand is passed by a separate suture passer.

16. The method of claim 15, wherein the suture passer is a suture lasso.

17. The method of claim 12, wherein the tissue is meniscus and the bone is tibia.

18. The method of claim 12, wherein the flexible strand is a braided suture comprising a plurality of high strength fibers.

19. The method of claim 12, wherein the flexible strand is a wire loop, a snare, or a stiff strand of ultrahigh molecular weight polyethylene.

20. The method of claim 12, wherein the flexible strand is a Nitinol wire loop.

21. The method of claim 12, wherein the shaft is formed of stainless steel.

22. The method of claim 12, wherein the flexible strand is released after passing through the tissue.

23. A combined tissue grasper and suture passing instrument, comprising:
a shaft extending along a longitudinal axis between a proximal end and a distal end;
a first jaw that is stationary relative to the shaft, the first jaw including a first through opening and a first transversal slot that extends from the first through opening but terminates prior to an outer circumference of the first jaw, wherein the first transversal slot is a through slot that extends entirely through both an upper surface and a lower surface of the first jaw and is configured to capture a suture within the first jaw, wherein the first transversal slot is narrower than the first through opening; and
a second jaw pivotally connected to the shaft, the second jaw including a second through opening and a second transversal slot extending from the second through opening to an outer circumference of the second jaw, wherein the second transversal slot is narrower than the second through opening and is configured to allow the suture to slide out of the second jaw from the second through opening.

24. A combined tissue grasper and suture passing instrument, comprising:
a shaft extending along a longitudinal axis between opposing end portions;
a lower jaw that is stationary relative to the shaft, the lower jaw including a first through opening and a first transversal slot that extends from the first through opening but terminates prior to a distal-most surface of the lower jaw,
wherein the first transversal slot is a through slot that extends entirely through both a lower surface and an upper surface of the lower jaw and is configured to capture a suture within the lower jaw,
wherein the first transversal slot is narrower than any portion of the first through opening;
wherein the first through opening is tear drop shaped;
wherein the first through opening and the first transversal slot are coaxial with one another along a first central longitudinal axis of the first jaw, and
an upper jaw pivotally connected to the lower jaw, the upper jaw including a second through opening and a second transversal slot extending from the second through opening through a distal-most surface of the upper jaw,
wherein the second transversal slot is narrower than any portion of the second through opening and is configured to allow the suture to slide out of the upper jaw from the second through opening.

* * * * *